(12) United States Patent
Jung et al.

(10) Patent No.: US 8,610,884 B2
(45) Date of Patent: Dec. 17, 2013

(54) METHOD FOR OPTICAL VISUALIZATION OF GRAPHENE DOMAINS (75) Inventors: Hee Tae Jung, Daejeon (KR); Yun Ho Kim, Chuncheon-si (KR); Dae Woo Kim, Gochang-gun (KR); Hyeon Su Jeong, Samcheok-si (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 28 days.

(21) Appl. No.: 13/498,798

(22) PCT Filed: Jan. 11, 2012

(86) PCT No.: PCT/KR2012/000248
§ 371 (c)(1),
(2), (4) Date: Mar. 28, 2012

(87) PCT Pub. No.: WO2013/094804
PCT Pub. Date: Jun. 27, 2013

(65) Prior Publication Data
US 2013/0162977 A1 Jun. 27, 2013

(30) Foreign Application Priority Data
Dec. 23, 2011 (KR) .................. 10-2011-0141160

(51) Int. Cl.
*G01N 1/00* (2006.01)

(52) U.S. Cl.
USPC ............................................ 356/36; 356/600

(58) Field of Classification Search
USPC .............. 356/36, 237.1, 239.1, 239.7, 237.2, 356/600; 438/14–18
See application file for complete search history.

(56) References Cited

U.S. PATENT DOCUMENTS 3,934,199 A * 1/1976 Channin ................. 324/762.03
5,311,137 A * 5/1994 Chang et al. ................. 324/501
5,394,098 A * 2/1995 Meyrueix et al. ........ 324/754.23
6,403,386 B1 * 6/2002 Liu ................................. 438/14
6,488,405 B1 * 12/2002 Eppes et al. ..................... 374/5
7,092,153 B1 * 8/2006 Atchison ....................... 359/395

FOREIGN PATENT DOCUMENTS

KR 10-2010-0112726 A 10/2010

OTHER PUBLICATIONS

Li, X. et al., "Large-Area Synthesis of High-Quality and Uniform Graphene Films on Copper Foils", Science, vol. 324, Jun. 5, 2009, pp. 1312-1314.
Foster, J. S. & Frommer, J. E., "Imaging of liquid crystals using a tunneling microscope", Nature, vol. 333, Jun. 1988, pp. 542-545.

(Continued)

*Primary Examiner* — Tarifur Chowdhury
*Assistant Examiner* — Michael P Lapage
(74) *Attorney, Agent, or Firm* — Knobbe, Martens, Olson & Bear, LLP (57) ABSTRACT The present invention relates to a method for optical visualization of graphene domains, and more particularly to a method for optical visualization of graphene domains, which can optically visualize the domains and domain boundaries of graphene by forming on a substrate a graphene layer to be measured, forming a liquid crystal layer on the formed graphene layer, and then measuring the optical properties of the formed nematic liquid crystal layer. The method for optical visualization of graphene domains according to the invention uses a liquid crystal-coating method, which is simpler and easier than a conventional method for observing graphene domains. Thus, the method of the invention is simple, time-saving and inexpensive and, at the same time, enables very-large-area graphene domains to be observed with a polarizing microscope or the like. Therefore, the inventive method will be very useful in the research of graphene's properties.

10 Claims, 6 Drawing Sheets

(56) References Cited

OTHER PUBLICATIONS

Smith, D. P. E. et al., "Smectic Liquid Crystal Monolayers on Graphite Observed by Scanning Tunneling Microscopy", Science, vol. 245, Jul. 7, 1989, pp. 43-45.

Hee-Tae Jung et al., "Direct visualization of large-area graphene domains and boundaries by optical birefringency", Nature Nanotechnology, Nov. 20, 2011, pp. 1-6.

* cited by examiner

METHOD FOR OPTICAL VISUALIZATION OF GRAPHENE DOMAINS

TECHNICAL FIELD

The present invention relates to a method for optical visualization of graphene domains, and more particularly to a method for optical visualization of graphene domains, which can optically visualize the domains and domain boundaries of graphene by forming on a substrate a graphene layer to be measured, forming a liquid crystal layer on the formed graphene layer, and then measuring the optical properties of the formed nematic liquid crystal layer.

BACKGROUND ART

In order to overcome the limitations of conventional silicon-based inorganic devices, advanced materials such as nanowires, carbon nanotubes and conductive polymers have been studied on various fields.

Particularly, graphene that was recently found is a planar sheet of carbons arranged in a hexagonal pattern and shows specific physical properties such as quantum hall effects. Also, a graphene layer has a very high electrical conductivity at a transmittance of 97.5%, and thus is expected to substitute for a transparent electrode of indium tin oxide. (ITO), the price of which is increasing rapidly. In addition, due to its flexible property, graphene can be used as transparent electrode materials and semiconductor materials in devices that are required in the industry.

The key to use graphene in industrial applications is to ensure technology for producing large amounts of graphene. A method of detaching graphene using a tape has the advantage of obtaining good quality graphene, graphene that is obtained by this method is only several micrometers in size, and thus cannot be used in industrial applications. In addition, a method of fabricating graphene sheets by dispersing graphite oxide (obtained by treating graphite with strong acid) in a solvent such as water causes problems, such as formation of various functional groups in graphene, which make it impossible to maintain the excellent electrical properties of graphene.

It is expected that a chemical vapor deposition (CVD) method of synthesizing graphene in a vapor phase using a catalyst such as copper (Cu) or nickel (Ni) can synthesize large amounts of good-quality graphene, and thus studies on the synthesis of good-quality graphene using this method are being actively conducted. However, graphene synthesized using the chemical vapor deposition method has a polycrystalline structure and shows inferior properties compared to graphene having a single-crystalline structure. This is because the domain boundaries of graphene greatly influence the electrical and mechanical properties of graphene.

As described above, it is very important to observe the domains and domain boundaries of graphene in order to synthesize graphene having ideal properties. However, conventional methods, including Raman 2D mapping, low-energy electron diffraction and transmittance electron microscopy, use expensive systems, require a large amount of time to observe graphene domains and are only effective for domains that are less than a few micrometers in size. Thus, there is a need for a method of observing the domains and domain boundaries of graphene in a general and easy way in order to control the properties of graphene.

Korean Patent Laid-Open Publication No. 2010-0112726 discloses a method capable of detecting the edge shape of graphene nanoribbons using an atom or a molecule, which shows higher adsorption energy at the zigzag edge of graphene than that at other portions. However, this method has problems in that the results of analysis can differ depending on whether the atom or the molecule is adsorbed, only the edge shape of graphene nanoribbons can be measured, and the measured edge shape of nanoribbons cannot be visualized.

Accordingly, the present inventors have made extensive efforts to observe the domains and domain boundaries of graphene in large area in a general and easy way and, as a result, have found that the domains and domain boundaries of graphene can be easily optically visualized by forming on a substrate a graphene layer to be measured, forming a liquid crystal layer on the formed graphene layer, and then measuring the optical properties of the formed liquid crystal layer, thereby completing the present invention.

DISCLOSURE OF INVENTION

A main object of the present invention is to provide a method for optical visualization of graphene domains, which is used to observe the domains and domain boundaries of graphene in large areas in a general and easy way.

To achieve the above object, the present invention provides a method for optical visualization of graphene domains, the method comprising the steps of: (a) forming on a substrate a graphene layer to be measured; (b) forming a liquid crystal layer on the formed graphene layer; and (c) measuring the optical properties of the formed liquid crystal layer, thereby visualizing the domains and domain boundaries of the graphene.

BRIEF DESCRIPTION OF THE DRAWINGS

FIG. 4 shows polarizing microscope images of graphene domains.

DESCRIPTION OF REFERENCE NUMERALS OF MAIN ELEMENTS USED IN THE DRAWINGS

| 5: substrate | 10: graphene |
|---|---|
| 15: liquid crystal | 20: cover substrate |

BEST MODE FOR CARRYING OUT THE INVENTION

Now, a preferred embodiment of the present invention will be descried hereinafter in more detail with reference to the accompanying drawings. In the following description, the detailed description on known function and constructions unnecessarily obscuring the subject matter of the present invention will be avoided hereinafter.

Throughout the specification, it will be understood that when a layer or element is referred to as being "on" another layer or element, it can be directly on the other layer or element, or one or more intervening layers may also be present between the two layers or elements. In addition, it will be understood that when a portion is referred to as "comprising" an element, it may further comprise other elements rather than excluding other elements, unless otherwise specified.

As used herein, the term "graphene layer" refers to a layer or sheet of a polycyclic aromatic molecule formed from a plurality of carbon atoms covalently bound to each other. The covalently bound carbon atoms may form a 6-membered ring as a repeating unit, or may further include at least one of a 5-membered ring and a 7-membered ring. Accordingly, in the graphene layer, the covalently bound carbon atoms (generally having sp2 hybridization) form a single layer. The graphene layer may have various structures which are determined according to the amount of the 5-membered rings and/or 7-membered rings which may be contained in the graphene. The graphene layer may be a single layer or a plurality of layers.

As used herein, the terms "about", "substantially", or any other version thereof, are defined as being close to the value as mentioned, when a unique manufacturing and material tolerance is specified. Such terms are used to prevent any unscrupulous invader from unduly using the disclosure of the present invention including an accurate or absolute value described to assist the understanding of the present invention.

As used herein, the term "optical properties" refers to optical properties that are changed by rearrangement of liquid crystal molecules when a nematic liquid crystal layer is formed on graphene so that the liquid crystal molecules are rearranged by an epitaxial effect. As used herein, the term "graphene layer to be measured" refers to graphene to be observed for domains and domain boundaries.

In one aspect, the present invention is directed to a method for optical visualization of graphene domains, the method comprising the steps of: (a) forming on a substrate a graphene layer to be measured; (b) forming a liquid crystal layer on the formed graphene layer; and (c) measuring the optical properties of the formed liquid crystal layer, thereby visualizing the domains and domain boundaries of the graphene.

Figure 1:
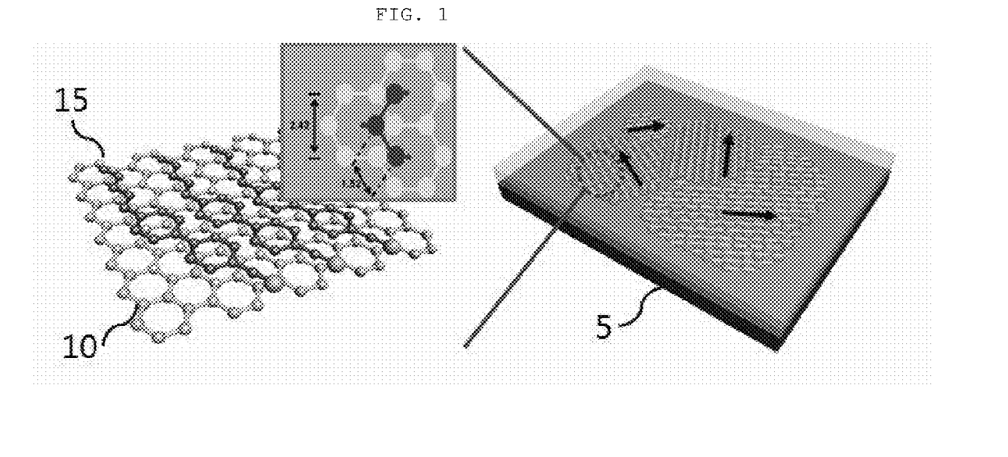
FIG. 1 is a schematic diagram showing a method for optical visualization of graphene domains according to the present invention.

Hereinafter, a method for optical visualization of graphene domains according to the present invention will be described in further detail. As shown in FIG. 1, graphene 10 to be measured is transferred onto a substrate 5 to form a graphene layer, and a layer of liquid crystals 15 is formed on the formed layer of the graphene 10, and after which the optical properties of the formed layer of the liquid crystals 15 are observed using a polarizing microscope or the like.

In other words, when plain graphene having no liquid crystal layer formed thereon is observed using a polarizing microscope, the shapes and boundaries of the graphene domains are not distinguished, because there is no change in the optical properties of the graphene. On the other hand, when a liquid crystal layer is formed on a graphene layer, the liquid crystal molecules of the liquid crystal layer are epitaxially rearranged along the graphene. Thus, when the formed liquid crystal layer is observed using a polarizing layer or the like, the domain shapes and boundaries of the graphene can be easily visually distinguished.

In the present invention, any flat substrate may be used as the substrate 5 without limitations of the transparency or material thereof, so long as it has no irregularities and thus does not distort the image of the liquid crystal layer formed on the graphene layer, Preferred examples of the substrate 5 include wafers, glass substrates, and polymer substrates such as a polyethyleneterephthalate (PET) substrate that is used as a flexible substrate.

In the present invention, examples of the layer of the graphene 10 to be measured include graphite consisting of a stack of graphene, single-layer graphene, multilayer graphene, graphene oxides, single-layer or multilayer graphene or graphite oxidation product such as graphite oxide, graphene fluoride, graphene having a functional group such as a sulfone group ($SO_3H$), functionalized graphite or a reduction product thereof, synthesized graphene or graphite, two-dimensional carbon allotropes of graphene or graphite such as graphene exfoliated from expanded graphite, singlemolecular, small-molecular or polymeric graphene or graphite such as didodecyldimethylammoniumbromide graphene, phenylisocyanate graphite oxide or alkylamine graphene, and graphene or graphite functionalized with particles such as silver (Au), platinum (Pt) or palladium (Pd).

The method for optical visualization of graphene domains according to the present invention relies on the interaction between the graphene surface and liquid crystal molecules, and thus it is important to maintain the graphene surface clean. For this reason, after the layer of the graphene 10 was transferred onto the substrate 5, it is heat-treated at a temperature of 200~600° C. for 1 minute to 1 hour in an atmosphere of inert gas such as argon or in a vacuum condition to remove impurities. If the graphene layer is heat-treated at a temperature lower than 200° C., removal of impurities from the graphene layer cannot be sufficiently achieved, and if the heat-treatment temperature is higher than 600° C., the substrate can be damaged.

To form the layer of the graphene 10, any method may be used without particular limitation, so long as it can form a uniform graphene layer on the substrate. Examples of a method that may be used to form the graphene layer in the present invention include a mechanical exfoliating method, a chemical exfoliation method, a chemical vapor deposition method, an epitaxial synthesis method, an organic synthesis method, etc. In a preferred embodiment, the layer of the graphene 10 may be formed by transferring graphene, grown by chemical vapor deposition or the like, on the substrate 10 using polydimethylsiloxane (PDMS), polymethylmethacrylate (PMMA), a heat release tape, a roll or the like.

Figure 2:
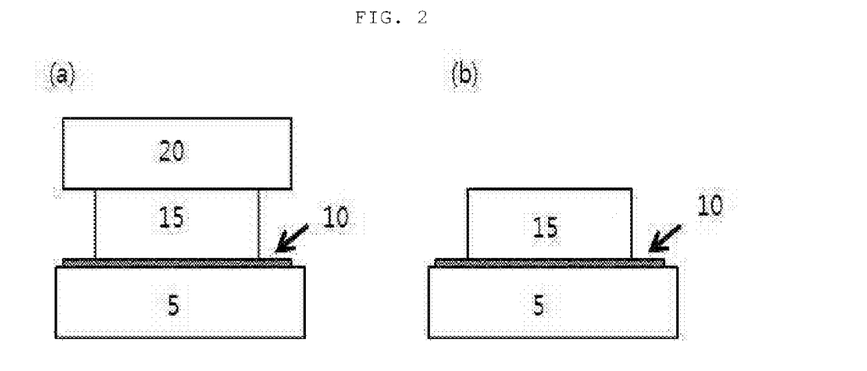
FIG. 2 schematically shows methods of forming a liquid crystal layer using a capillary method (a) and a spin-coating method (b).

On the layer of the graphene 10 formed on the substrate as described above, the layer of the liquid crystals 15 is formed. To form the layer of the liquid crystals 15, any method may be used without limitation, so long as it can form the liquid layer uniformly on the graphene layer. Preferably, the method of forming the liquid crystal layer is selected from the group consisting of a drop-coating method, a spin-coating method, a low-temperature vapor deposition method, a method of injecting a liquid crystal into a sandwich cell, a doctor blade method, a paint brushing method, a spray-coating method, a dip coating method. More preferably, the spin-coating method (FIG. 2a) may be used to form the liquid crystal layer on the graphene layer, or the method of injecting a liquid crystal into a sandwich cell (FIG. 2b) may also be used which comprises injecting a liquid crystal into the fabricated sandwich cell by the capillary phenomenon between the graphene layer and the cover substrate 10.

Herein, the thickness of the liquid crystal layer is determined according to the birefringence value of the liquid crystal material used. In order to optically observe the domain boundaries of graphene through the oriented liquid crystal layer in the visible light region, the thickness of the liquid crystal layer is preferably in the range of 300 nm to 100 µm. If the thickness of the liquid crystal layer is less than 300 nm, the birefringence value thereof will be too low to distinguish the color, and it can be influenced not only by liquid crystal orientation caused by the graphene surface, but also liquid crystal orientation caused by air. On the other hand, if the thickness of the liquid crystal layer is more than 100 µm, it will be difficult to observe a color by birefringence.

The liquid crystal of the liquid crystal layer may be any nematic liquid crystal whose liquid crystal molecules can be rearranged according to the orientation of graphene domains. Preferably, the nematic liquid crystal may be any nematic liquid crystal having an alkyl group of 2-30 carbon atoms or a benzene ring. More preferably, the nematic liquid crystal is selected from the group consisting of 4-phetyl-4'-cyanobiphenyl, 4-octyl-4'-cyanobiphenyl, ZOC-5162XX-2 (Chisso Co., Ltd., Japan), ZOC162XX-5 (Chisso Co., Ltd., Japan), CH-100 (Shichem Co., Ltd., China), and mixtures thereof.

The alkyl group of the nematic liquid crystal matches with the gap between the zigzag portions of the hexagonal structures of the graphene layer. Thus, the liquid crystal molecules having an alkyl group are epitaxially rearranged and anchored a suitable direction on the graphene surface according to the domain orientation of the graphene layer. Also, the benzene ring structure contained in the liquid crystal molecules strongly interacts with the graphene surface having a hexagonal honeycomb structure consisting of sp2-hybridized carbon atoms. Thus, the birefringence of light is changed by the liquid crystal molecules anchored according to the domain orientation of graphene, and as a result, the liquid crystal layer changes color depending on the graphene domain, whereby the graphene domains can be optically visualized.

To measure the optical properties of the rearranged liquid crystal layer, any method or system of measuring the optical properties using polarized light may be used without limitation. Preferably, a polarizing microscope which can perform observation over a wide range may be used to observe and measure the optical properties of the liquid crustal layer rearranged according to the domain orientation of graphene.

Thus, the method for optical visualization of graphene domains according to the invention uses a liquid crystal-coating method, which is simpler and easier than a conventional method for observing graphene domains. Thus, the method of the invention is simple, time-saving and inexpensive and, at the same time, enables very-large-area graphene domains to be observed with a polarizing microscope or the like. Therefore, the inventive method will be very useful in the research of graphene's properties.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Measurement of Graphene Domains 1-1: Synthesis and Transfer of Graphene

Figure 3:
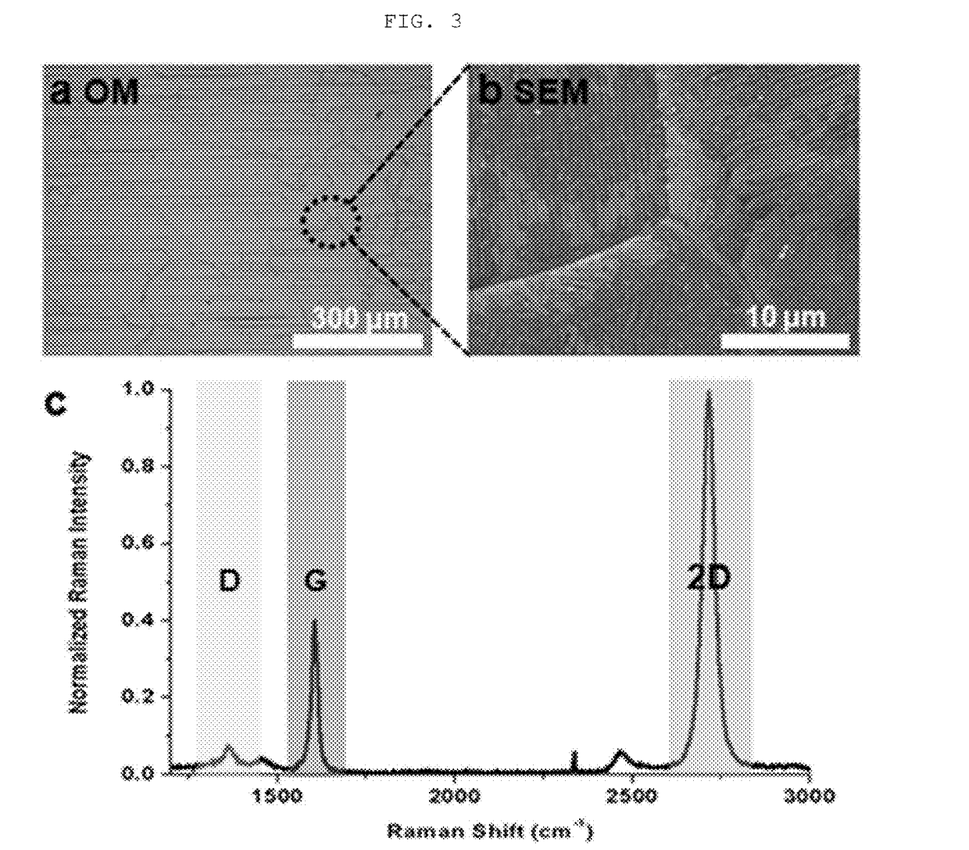
FIG. 3 shows a 200× magnification OM image (a), a 10,000× magnification SEM image (b) and a Raman spectrum graph for a graphene transferred onto an $SiO_2$/Si substrate (c), measured for a graphene fabricated according to the method of the present invention.

Graphene was synthesized using the chemical vapor deposition (CVD) reported by Li et al. (Li, X. et al., Large-area synthesis of high-quality and uniform graphene films on copper foils, *Science*, 324, 1312-1314, 2009). First, a copper (Cu) foil was inserted into a quartz tube, and then heated to 1,000° C. while hydrogen was allowed to flow at a rate of 10 sccm under a pressure of 90 mtorr. As the copper foil reached 1,000° C., it was annealed under the above conditions for 2 hours, and methane ($CH_4$) and hydrogen ($H_2$) were passed through the quartz tube for 30 minutes at rates of 30 sccm and 10 sccm, respectively. Finally, the copper foil was cooled rapidly to room temperature at a pressure of 90 mtorr in a hydrogen atmosphere, thereby growing graphene (FIG. 3). In order to produce a support layer for the graphene transferred onto the substrate, PMMA was spin-coated on the grown graphene, and the copper foil was removed using a liquid etchant ($FeCl_3$). Next, the graphene/PMMA film was washed to remove the remaining etchant, and then transferred onto a glass or $SiO_2$/Si substrate. Then, the PMMA of the transferred graphene/PMMA film was removed using acetone. The remaining PMMA or other impurities on the graphene were washed out with acetone, and then the graphene was heat-treated at 400° C. for 30 minutes.

1-2: Formation of Liquid Crystal Layer 4-pentyl-4'-cyanobiphenyl (hereinafter referred to as 5CB) was spin-coated on the graphene obtained in Example 1-1. Also, a cover substrate was provided above the graphene, and then 5CB was injected between the graphene obtained in Example 1-1 and the cover substrate by using a capillary phenomenon. As a result, the thicknesses of the formed liquid crystal layers were 2 µm, 5 µm and 10 µm.

1-3: Observation of Optical Properties of Liquid Crystal Layer

In order to evaluate the optical properties of the 5 µm-thick 5CB layer spin-coated on the graphene layer on the SiO2/Si substrate in Example 1-2, the optical properties of the 5CB layer were measured using a polarizing microscope (LV 100-POL, Nikon) equipped with a hot stage. Also, in order to measure the orientation of the 5CB molecules on the graphene, 5CB coated on the graphene layer on the SiO2/Si substrate in Example 1-2 was mounted on a rotatable stage of a polarizing microscope such that it was perpendicular to the diffusion direction of light, and then the optical properties thereof were measured.

Figure 4:
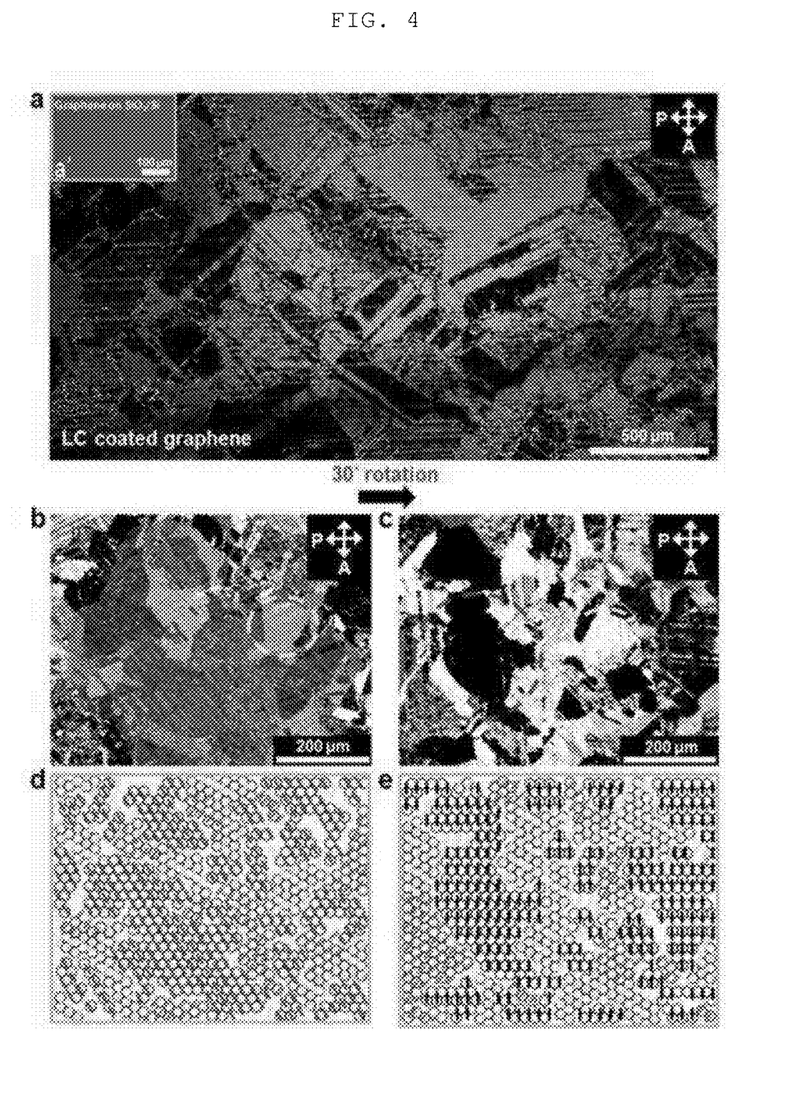
In FIG. 4, (a): an image of a liquid crystal layer formed on graphene; (a'): an image of graphene having no liquid crystal layer formed thereon; (b) and (c): images taken before and after a liquid crystal layer formed on graphene is rotated by an angle of 30°; and (d) and (e): schematic diagrams of (b) and (c).

As a result, as can be seen in FIG. 4a', in the graphene layer on the $SiO_2$/Si substrate, which was not coated with 5CB, the domain shapes and boundaries of the graphene were not distinguished, whereas 5CB spin-coated on the graphene layer on the SiO$_2$/Si substrate (FIG. 4a) changed depending on the domain direction of the graphene, whereby the domains and domain boundaries of the graphene could be easily distinguished. In addition, graphene domains having a size of more than 200 μm could also be easily distinguished.

As shown in FIG. 4b, the liquid crystal layer formed on the graphene showed mosaic-like structures having distinguishable boundaries which were distinguished by different colors, and domains showing the same color showed the same change in birefringence upon rotation. As shown in FIG. 4c, when the liquid crystal layer was rotated by an angle of 30° in a clockwise direction, green domains having red circles corresponding to low birefringence dark color and showed the lowest intensity. This suggests that liquid crystal molecules are oriented on an analyzer or a polarizing plate. Also, the red domains shown in FIG. 4b turned a light white color after 30° rotation.

Meanwhile, FIGS. 4d and 4e show schematic diagrams of the orientation of liquid crystal molecules on the surface of the multi-domain graphene, taken by a polarizing microscope. It could be seen that the motivation for the change in the orientation of nematic liquid crystals, induced by the multiple domains of graphene, is attributable to the presence of strong liquid crystal molecule-graphene interactions. It was reported that the hexagons present in the graphene plane might induce highly ordered packing of liquid crystals containing cyanobiphenyl groups and alkyl tails, by very strong n-stacking interactions (Foster, J. S. & Frommer, J. E., Imaging of liquid crystals using a tunneling microscope. *Nature*, 333, 542-545, 1988; Smith, D. P. E., Horber, H., Gerber, C. & Binning, G. Smectic liquid crystal monolayers on graphite observed by scanning tunneling microscopy, *Science*, 245, 43-45, 1989).

Test Example 1

Observation of Optical Properties Using Various Kinds of Liquid Crystals

In order to measure the domains and domain boundaries using various kinds of liquid crystals, each of ZOC-5162XX-2 (Chisso, Japan), ZOC-5162XX-5 (Chisso, Japan) and CH-100 (Slichem, China), which are commercially available, was spin-coated on a graphene layer to a thickness of 5 μm in the same manner as in Example 1 to form liquid crystal layers. The optical properties of the formed liquid crystal layers were measured using a polarizing microscope equipped with a hot stage.

Figure 5:
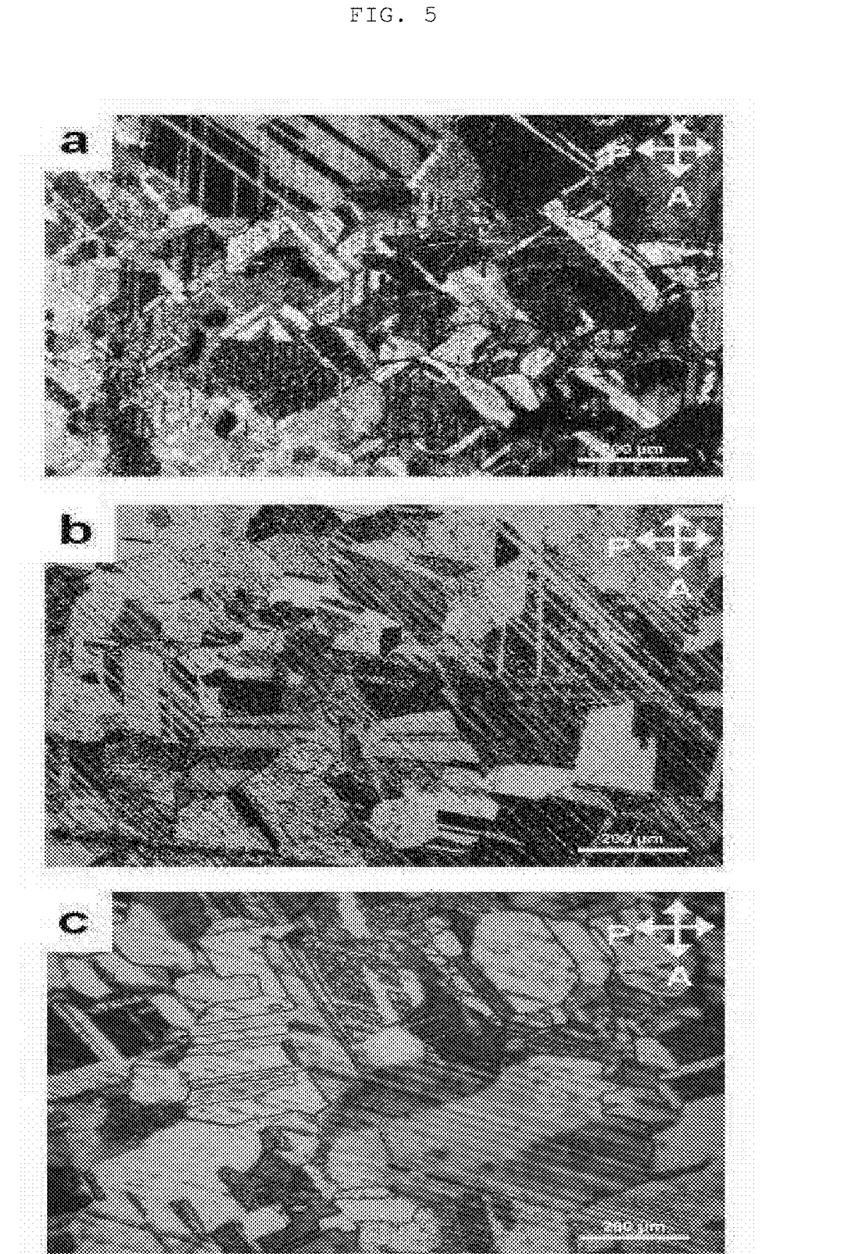
FIG. 5 shows polarizing microscope images of graphene domains observed using liquid crystal materials of ZOC-5162XX-2(a), ZOC-5162XX-5(b) and CH-100(c).

As a result, as can be seen in FIG. 5, the domains of graphene could be easily visually observed using not only the above-described 5CB, but also ZOC-5162XX-2 (Chisso, Japan) (FIG. 5a), ZOC-5162XX-5 (Chisso, Japan) (FIG. 5b) and CH-100 (Slichem, China) (FIG. 5c).

Test Example 2

Figure 6:
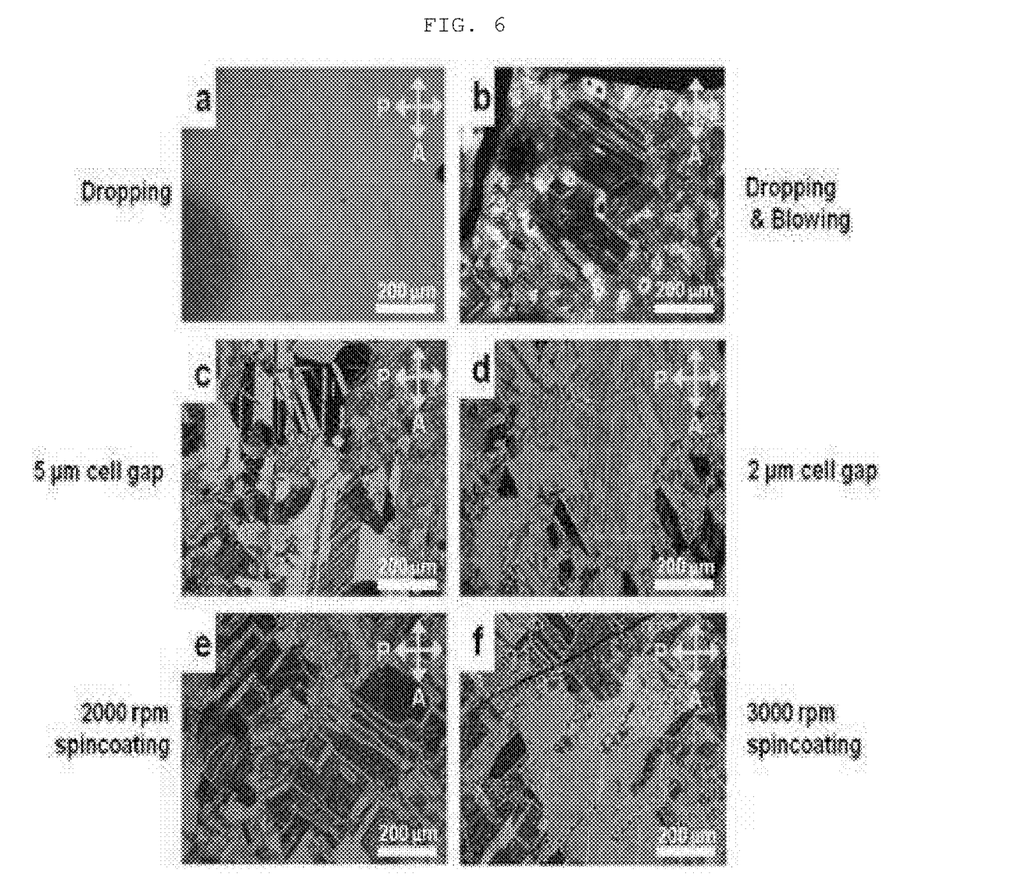
FIG. 6 shows polarizing microscope images of liquid crystal layers formed on a graphene layer using a drop-coating method (a), a drop-coating/nitrogen gas blowing method (b), a method of injecting a liquid crystal into a sandwich cell having a gap of 5 μm (c) or 2 μm (d) between graphene and a cover substrate, and a spin coating method having a rotating speed of 2000 rpm (e) or 3000 rpm (f).
Figure 7:
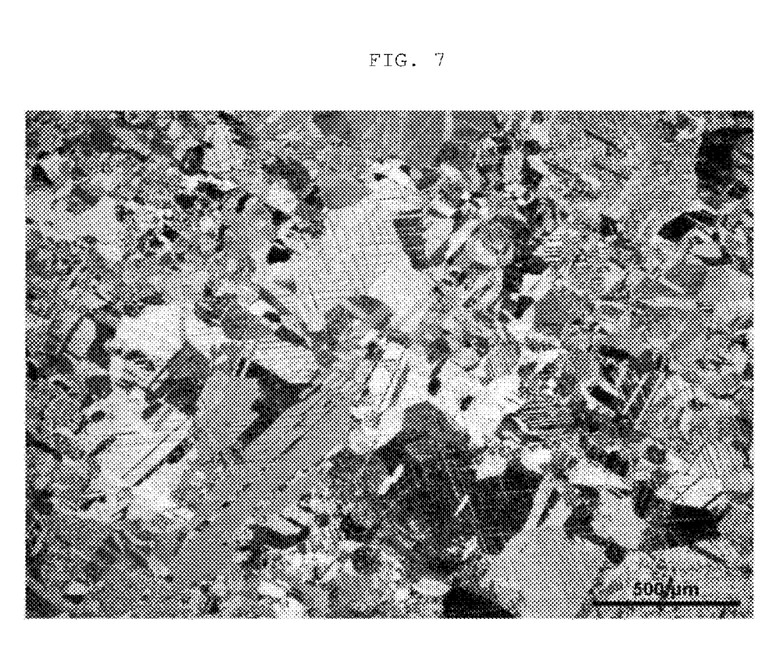
FIG. 7 is a polarizing microscope image of a liquid crystal layer formed on a graphene layer using a method of injecting a liquid crystal into a sandwich cell having a gap of 10 μm between graphene and a cover substrate.

Observation of Optical Properties Using Various Methods for Forming Liquid Crystal Layer In order to measure the domains and domain boundaries of graphene using various methods for forming a liquid crystal layer, a liquid crystal layer was formed in the same manner as in Example 1 using each of a method of drop-coating a liquid crystal on a graphene layer (FIG. 6a), a method of drop-coating a liquid crystal and then blowing nitrogen gas (FIG. 6b), a method of injecting a liquid crystal into a sandwich cell having a gap of 5 μm (FIG. 6c), 2 μm (FIG. 6d) or 10 μm (FIG. 7) between the graphene and the cover substrate, and a spin-coating method having a rotating speed of 2000 rpm (FIG. 6e) or 3000 rpm (FIG. 6f). The optical properties of the liquid crystal layer formed on the graphene layer by each of the above-described methods were measured using a polarizing microscope (LV 100-POL, Nikon) equipped with a hot stage.

As a result, as can be seen in FIG. 6, the liquid crystal layer could be formed on the graphene layer by various methods. Also, it could be seen that it is important to coat a liquid crystal uniformly on the graphene layer to a suitable thickness in order to observe the accurate domains and domain boundaries of graphenes.

Test Example 3

Observation of Optical Properties Using Various Substrates

In order to measure the domains and domain boundaries of graphene using various substrates, a liquid crystal layer formed in the same manner as in Example 1 using a substrate made of glass or polyethyleneterephthalate (PET). The optical properties of the formed liquid crystal layer were measured using a polarizing microscope (LV 100-POL, Nikon) equipped with a hot stage.

Figure 8:
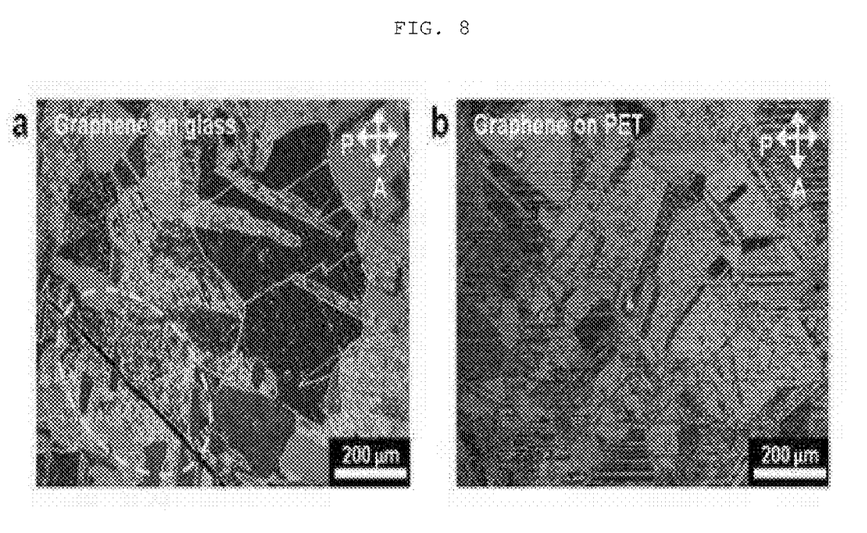
FIG. 8 shows polarizing microscope images of graphene domains observed using a glass substrate (a) and a PET substrate (b).

As a result, as can be seen in FIG. 8, the domains of graphene could be measured using not only the glass substrate, but also the PET substrate. This suggests that various substrates that do not distort the image of liquid crystals can be used to measure the domains of graphene.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

The method for optical visualization of graphene domains according to the invention uses a liquid crystal-coating method, which is simpler and easier than a conventional method for observing graphene domains. Thus, the method of the invention is simple, time-saving and inexpensive and, at the same time, enables very-large-area graphene domains to be observed with a polarizing microscope or the like. Therefore, the inventive method will be very useful in the research of graphene's properties.

What is claimed is:

1. A method for optical visualization of graphene domains, the method comprising the steps of:
   (a) forming a graphene layer on a substrate to be measured;
   (b) forming a liquid crystal layer on the formed graphene layer; and
   (c) measuring the optical properties of the formed liquid crystal layer, thereby visualizing the domains and domain boundaries of the graphene.

2. The method of claim 1, wherein the substrate is selected from the group consisting of glass, polymer, semiconductor, and combination of thereof.

3. The method of claim 1, wherein the liquid crystal of the liquid crystal layer is a nematic liquid crystal.

4. The method of claim 3, the nematic liquid crystal is the nematic liquid crystal having an alkyl group of 2-30 carbon atoms or a benzene ring.

5. The method of claim 1, wherein the step (a) further comprise heat-treating the layer of the graphene to be measured to remove impurities after forming the layer of the graphene to be measured on the substrate.

6. The method of claim 5, the heat-treating is performed at a temperature of 200~600° C. for 1 minute to 60 minutes.

7. The method of claim 1, the thickness of the liquid crystal layer in the step (b) is in the range of 300 nm to 100 μm.

8. The method of claim 1, wherein the optical properties of the liquid crystal layer in the step (c) is measured using polarized light.

9. The method of claim 1, the method of forming the layer of the liquid crystals in the step (b) is selected from the group consisting of a drop-coating method, a spin-coating method, a low-temperature vapor deposition method, a method of injecting a liquid crystal into a sandwich cell, a doctor blade method, a paint brushing method, a spray-coating method and a dip coating method.

10. The method of claim 1, the liquid crystal layer in the step (b) is formed epitaxially rearranging liquid crystal molecules on a surface of graphene.

\* \* \* \* \*